US00PP19672P2

(12) United States Plant Patent
Ruys

(10) Patent No.: US PP19,672 P2
(45) Date of Patent: Feb. 3, 2009

(54) ***MANDEVILLA* PLANT NAMED 'SUNPARABENI'**

(50) Latin Name: *Mandevilla hybrida*
Varietal Denomination: Sunparabent

(75) Inventor: Theo Ruys, Leimuiderbrug (NL)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/012,485

(22) Filed: Jan. 31, 2008

(51) Int. Cl.
*A01H 5/00* (2006.01)

(52) U.S. Cl. ..... Plt./232
(58) Field of Classification Search ..... Plt./232
See application file for complete search history.

*Primary Examiner*—Kent L Bell
*Assistant Examiner*—Georgia Helmer
(74) *Attorney, Agent, or Firm*—C. A. Whealy

(57) ABSTRACT

A new and distinct cultivar of *Mandevilla* plant named 'Sunparabeni', characterized by its upright and vining plant habit; relatively small glossy foliage; freely flowering habit; red purple-colored flowers; and long flowering period.

2 Drawing Sheets

Botanical designation: *Mandevilla hybrida.*
Cultivar denomination: 'Sunparabeni'.

REFERENCED TO RELATED APPLICATIONS:

Title: *Mandevilla* Plant Named 'Sunparapibra' Applicant: Theo Ruys Serial number: Filed concurrently with this application Title: *Mandevilla* Plant Named 'Sunparavel' Applicant: Theo Ruys Serial number: Filed concurrently with this application

BACKGROUND OF THE INVENTION

The present invention relates to a new and distinct cultivar of *Mandevilla,* botanically known as *Mandevilla hybrida* and hereinafter referred to by the name 'Sunparabeni'.

The new *Mandevilla* is a naturally-occurring branch mutation of the *Mandevilla hybrida* cultivar Sunmandecrim, disclosed in U.S. Plant Pat. No. 15,539. The new *Mandevilla* was discovered and selected by the Inventor from within a population of plants of the cultivar Sunmandecrim in a controlled environment in Amstelveen, The Netherlands in March, 2005.

Asexual reproduction of the new cultivar by cuttings in Leimuiderbrug, The Netherlands, since April, 2005, has shown that the unique features of this new *Mandevilla* are stable and reproduced true to type in successive generations.

SUMMARY OF THE INVENTION

Plants of the cultivar Sunparabeni have not been observed under all possible environmental conditions. The phenotype may vary somewhat with variations in environment such as temperature and light intensity without, however, any variance in genotype.

The following traits have been repeatedly observed and are determined to be the unique characteristics of 'Sunparabeni'. These characteristics in combination distinguish 'Sunparabeni' as a new and distinct cultivar:

1. Upright and vining plant habit.
2. Relatively small glossy foliage.
3. Freely flowering habit.

4. Dark red-colored flowers.
5. Long flowering period.

Plants of the new *Mandevilla* differ primarily from plants of the parent, the cultivar Sunmandecrim, in flower color as plants of the cultivar Sunmandecrim have lighter red-colored flowers.

Plants of the new *Mandevilla* can be compared to plants of the *Mandevilla* cultivar Sunparapibra, disclosed in a U.S. Plant Patent application filed concurrently, and the *Mandevilla* cultivar Sunparavel, disclosed in a U.S. Plant Patent application filed concurrently. Plants of the new *Mandevilla* differ primarily from plants of the cultivars Sunparapibra and Sunparavel in flower color.

Plants of the new *Mandevilla* can also be compared to plants of the *Mandevilla* cultivar Sunmandecos, disclosed in U.S. Plant Pat. No. 15,202. In side-by-side comparisons conducted in Higashiomi, Shiga, Japan, plants of the new *Mandevilla* differed from plants of the cultivar Sunmandecos in the following characteristics:

1. Plants of the new *Mandevilla* had shorter leaves than plants of the cultivar Sunmandecos.
2. Plants of the new *Mandevilla* were more freely flowering than plants of the cultivar Sunmandecos.
3. Plants of the new *Mandevilla* and the cultivar Sunmandecos differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Mandevilla.*

The photograph on the first sheet comprises a side perspective view of a typical flowering plant of 'Sunparabeni' grown in a container.

The photograph on the second sheet is a close-up view of typical flowers and flower buds of 'Sunparabeni'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the summer in an outdoor nursery in Higashiomi, Shiga, Japan for about five months. During the production of the plants, day temperatures averaged 25° C. and night temperatures averaged 15° C.

Botanical classification: *Mandevilla hybrida* cultivar Sunparabeni.

Parentage: Naturally-occurring branch mutation of the *Mandevilla hybrida* cultivar Sunmandecrim, disclosed in U.S. Plant Pat. No. 15,539.

Propagation:

*Type.*—By vegetative cuttings.

*Time to initiate roots.*—About two weeks at 23° C. to 25° C.

*Time to produce a rooted young plant.*—About 40 days at 23° C. to 25° C.

*Root description.*—Fibrous, fleshy; light brown in color.

*Rooting habit.*—Freely branching.

Plant description:

*Form.*—Perennial. Upright and vining plant habit. Vigorous growth habit.

*Plant height.*—About 172 cm.

*Lateral branch description.*—Length: About 172 cm. Diameter: About 2.7 mm. Internode length: About 18.4 cm. Strength: Strong. Texture: Smooth, glabrous. Color: 144A overlain with 178A.

Foliage description:

*Arrangement.*—Opposite, simple.

*Length.*—About 7.6 cm.

*Width.*—About 4.3 cm.

*Shape.*—Elliptic.

*Apex.*—Cuspidate.

*Base.*—Rounded to cordate.

*Margin.*—Entire.

*Texture, upper and lower surfaces.*—Smooth, glabrous.

*Luster, upper and lower surfaces.*—Glossy.

*Venation pattern.*—Pinnate, reticulate.

*Color.*—Developing foliage, upper surface: 137B. Developing foliage, lower surface: 144A. Fully expanded foliage, upper surface: 139A; venation, 145D. Fully expanded foliage, lower surface: 146A; venation, 145D.

*Petiole length.*—About 1.7 cm.

*Petiole diameter.*—About 1.7 mm.

*Petiole texture, upper and lower surfaces.*—Smooth, glabrous.

*Petiole color, upper and lower surfaces.*—145D.

Flower description:

*Flower type and habit.*—Single salverform flowers; flowers racemose; flowers face mostly outwardly. Flowers not persistent. Freely flowering habit, about five flowers per inflorescence.

*Natural flowering season.*—Long flowering period; summer to late autumn in Japan; flowering continuous during this period.

*Flower longevity on the plant.*—About seven to ten days.

*Fragrance.*—None detected.

*Inflorescence length.*—About 13 cm.

*Inflorescence diameter.*—About 13 cm.

*Flowers.*—Appearance: Flared trumpet, corolla fused, five-parted; petals imbricate; flowers roughly star-shaped. Diameter: About 8 cm. Depth (length): About 7.8 cm.

*Flower buds.*—Height: About 7.7 cm. Diameter: About 1.3 cm. Shape: Oblong. Color: 60A.

*Corolla.*—Arrangement/appearance: Single whorl of five petals, fused into flared trumpet; petals imbricate. Petal length: About 3.9 cm. Petal width: About 2.7 cm. Petal shape: Spatulate. Petal apex: Acuminate. Petal margin: Entire, undulate. Petal texture, upper and lower surfaces: Smooth, glabrous. Color: Petal, when opening, upper surface: N57A. Petal, when opening, lower surface: 53D. Petal, fully opened, upper surface: 58B; color becoming closer to 55A with development. Petal, fully opened, lower surface: 53D. Tube: 54D. Throat: N25A.

*Sepals.*—Arrangement/appearance: Five per flower in a single whorl; fused. Length: About 8.6 mm. Width: About 1.5 mm. Shape: Lanceolate. Apex: Aristate. Margin: Entire. Texture, upper and lower surfaces: Smooth, glabrous. Color, immature, upper surface: 145C. Color, immature, lower surface: 145B. Color, mature, upper and lower surfaces: 145C.

*Peduncles.*—Length: About 4.1 cm. Diameter: About 1.8 mm. Texture: Smooth, glabrous. Strength: Flexible, but strong. Color: 144A.

*Pedicels.*—Length: About 1.9 cm. Diameter: About 2.1 mm. Texture: Smooth, glabrous. Strength: Flexible, but strong. Color: 144B.

*Reproductive organs.*—Stamens: Quantity/arrangement: Typically five; filaments fused to corolla; anthers, connivent. Anther shape: Lanceolate. Anther size: About 1 cm by 1 mm. Anther color: 11C. Pollen amount: Scarce. Pollen color: 155B. Pistils: Quantity: Typically one. Pistil length: About 2.5 cm. Stigma shape: Conical. Stigma color: 145D. Style length: About 2.5 cm. Style color: 145D. Ovary color: 144C.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 4° C. to about 30° C.

It is claimed:

1. A new and distinct *Mandevilla* plant named 'Sunparabeni' as illustrated and described.

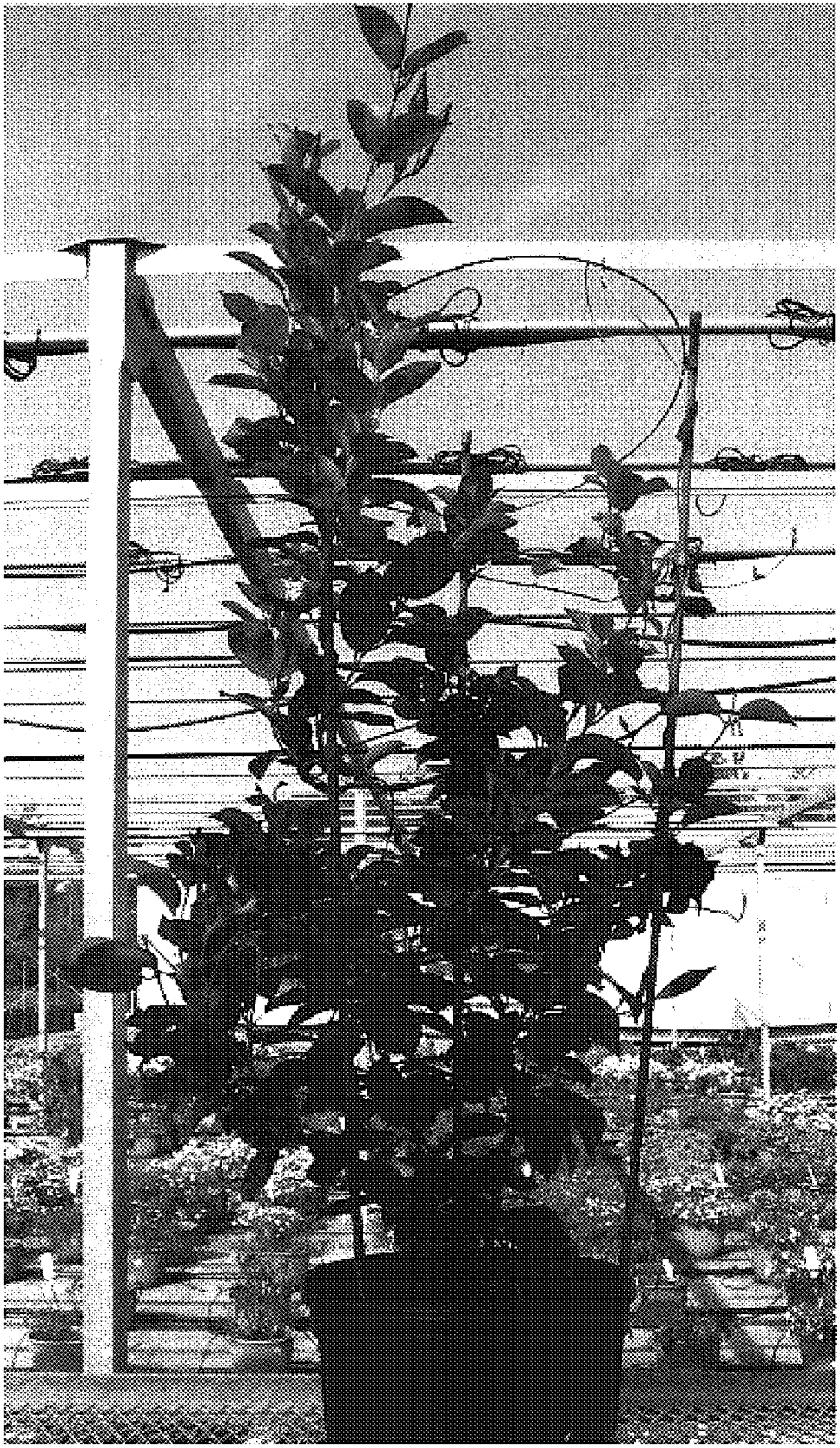

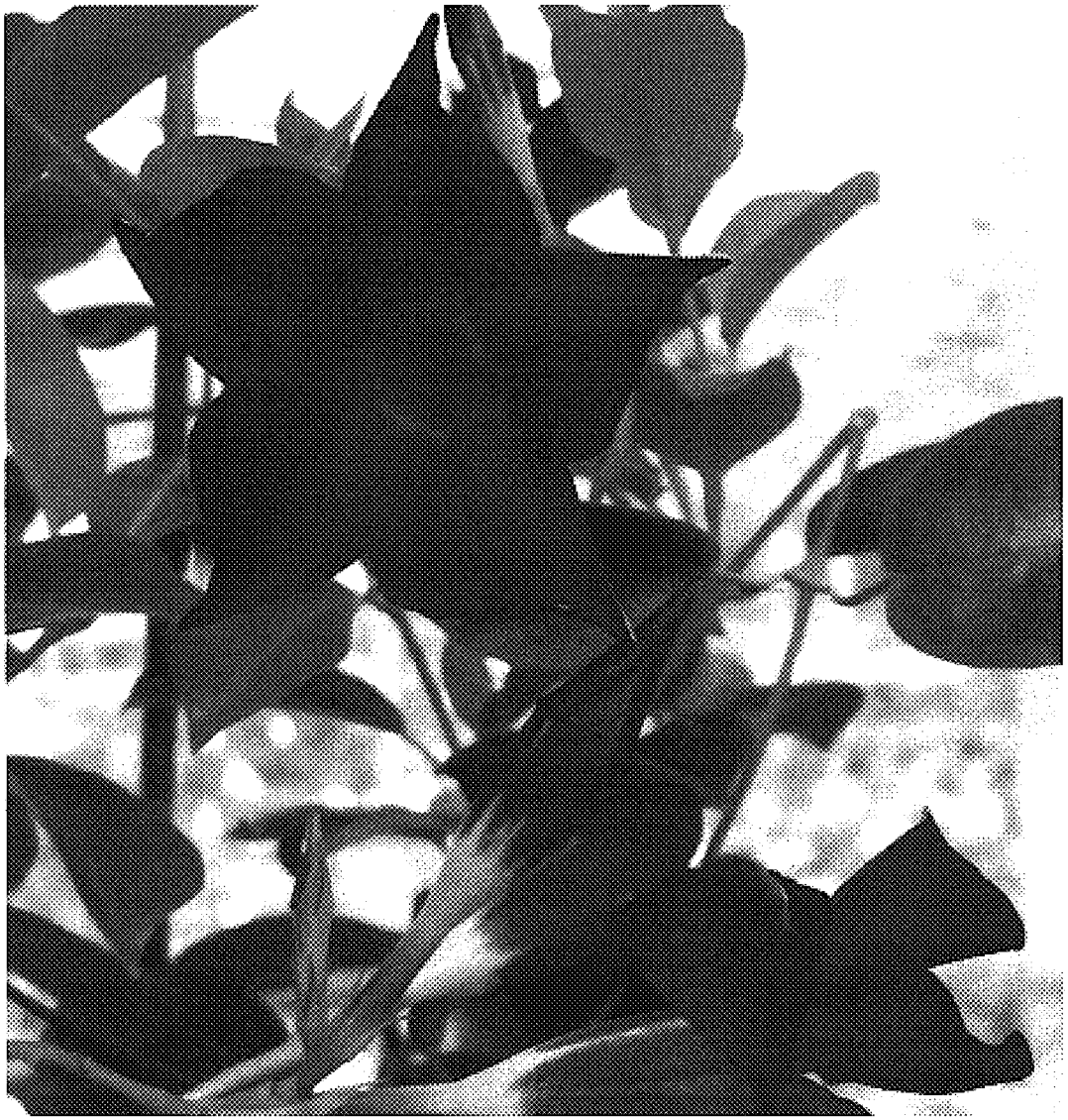

* * * * *